United States Patent [19]

Jakobsen et al.

[11] Patent Number: 4,970,232
[45] Date of Patent: Nov. 13, 1990

[54] ARYLOXYPHENYLPROPYLAMINES AND THEIR PREPARATION AND USE

[75] Inventors: Palle Jakobsen, Vaerløse; Jørgen Drejer, Brønshøj, both of Denmark

[73] Assignee: A/S Ferrosan, Søborg, Denmark

[21] Appl. No.: 473,862

[22] Filed: Feb. 2, 1990

Related U.S. Application Data

[62] Division of Ser. No. 277,561, Nov. 29, 1988.

[30] Foreign Application Priority Data

Dec. 1, 1987 [DK] Denmark .............................. 6309/87

[51] Int. Cl.$^5$ ...................... A61K 31/36; A61K 31/35
[52] U.S. Cl. .................................... 514/466; 514/651; 549/437; 564/355
[58] Field of Search ................................ 514/466, 651

[56] References Cited

U.S. PATENT DOCUMENTS 4,296,126 10/1981 Nedelec et al. ..................... 514/651
4,508,732 4/1985 Hausberg et al. ................... 514/466

OTHER PUBLICATIONS

Yoshida et al, "Studies on Aromatic Basic Ethers, etc.", pp. 508-518, vol. 93, 1973.

Primary Examiner—Glennon H. Hollrah
Attorney, Agent, or Firm—Gordon W. Hueschen

[57] ABSTRACT

Novel aryloxyphenylpropylamines having the formula

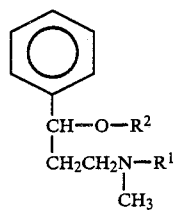

wherein
$R^1$ is $C_{3-7}$-cycloalkyl, $C_{3-10}$-alkyl, or alkenyl which may be straight, branched or cyclic, unsubstituted or substituted with $C_{1-4}$-alkoxy, aryloxy or cycloalkyl or cycloalkylalkyl; and
$R^2$ is 3,4-methylenedioxyphenyl, aryl or heteroaryl, which are optionally substituted with one or more cyano, halogen, $C_{1-6}$-alkyl, $C_{1-6}$-alkoxy, $C_{1-6}$-alkenyl, trifluoromethyl, $C_{3-5}$-alkylene, aryloxy or aralkoxy and a salt thereof with a pharmaceutically acceptable acid.

The novel compounds are useful in the treatment of anoxia, migraine, ischemia and epilepsy.

6 Claims, No Drawings

ARYLOXYPHENYLPROPYLAMINES AND THEIR PREPARATION AND USE

This is a division of application Ser. No. 07/277,561, filed Nov. 29, 1988, now pending.

The present invention relates to therapeutically active aryloxyphenylpropylamines, a method of preparing the same and to pharmaceutical compositions comprising the compounds. The novel compounds are useful in the treatment of anoxia, ischemia, migraine and epilepsy.

It is well known that accumulation of calcium in the brain cells (calcium overload) is seen after periods of uncontrolled hyperactivity in the brain, such as after convulsions, migraine, anoxia and ischemia. As the concentration of calcium in the cells is of vital importance for the regulation of cell function, an uncontrolled high concentration of the cell calcium will lead to, or indirectly cause the symptoms and possibly also the degenerative changes combined with the above diseases.

Therefore calcium overload blockers selective for brain cells will be useful in the treatment of anoxia, ischemia, migraine and epilepsy.

Well known calcium antagonists such as nifedipine, verapamil and diltiazem have activity against pheripheral calcium uptake, e.g. in blood vessels and the heart, however have shown only very low activity against calcium overload in brain cells.

Accordingly it is an object of the invention to provide novel compounds having activity against calcium overload in brain cells.

The novel compounds of the invention are aryloxyphenylpropylamines having the general formula I

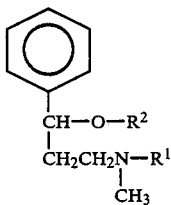

(I)

wherein
R$^1$ is C$_{3-7}$-cycloalkyl, C$_{3-10}$-alkyl, or alkenyl which may be straight, branched or cyclic, unsubstituted or substituted with C$_{1-4}$-alkoxy, aryloxy or cycloalkyl or cycloalkylalkyl; and
R$^2$ is 3,4-methylenedioxyphenyl, aryl or heteroaryl, which are optionally substituted with one or more cyano, halogen, C$_{1-6}$-alkyl, C$_{1-6}$-alkoxy, C$_{2-6}$-alkenyl, trifluoromethyl, C$_{3-5}$-alkylene, aryloxy or aralkoxy and a salt thereof with a pharmaceutically acceptable acid.

Examples of such salts include inorganic and organic acid addition salts such as hydrochloride, hydrobromide, sulphate, phosphate, acetate, fumarate, maleate, citrate, lactate, tartrate, oxalate, or similar pharmaceutically-acceptable inorganic or organic acid addition salts.

The invention also relates to a method of preparing the above mentioned compounds. This methods comprises (a) reacting a compound having the general formula II

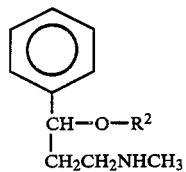

(II)

wherein R$^2$ has the meaning defined above, with a compound having the the general formula R$^1$—X, wherein X is a leaving group such as halogen and R$^1$ has the meaning defined above, and (b) reacting a compound having the formula III

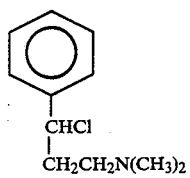

(III)

with a compound having the formula IV $$R^2O\ H \qquad\qquad (IV)$$

wherein R$^2$ has the meaning defined above, giving compounds of the general formula V

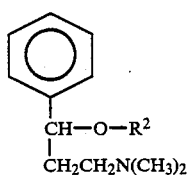

(V)

and (c) preparing compounds having the formula III from the corresponding hydroxy compound by means of SOCl$_2$. The hydroxy compounds being prepared by a NaBH$_4$ reduction of the corresponding oxo-compound, which is prepared by a Mannich reaction (d) preparing compounds of the general formula II by demethylating compounds of the general formula V by means of ClCOOCHClCH$_3$.

The pharmacological properties of the compounds of the invention can be illustrated by determining their capability to inhibit calcium uptake into brain synaptosomes.

PRINCIPLE

Depolarization of neuronal membranes leads to an opening of socalled 'voltage operated calcium channels' (VOC) in the membranes which allows a massive influx of calcium from the extracellular space. A crude synaptosomal preparation (socalled P$_2$ fraction) contains small vesicles surrounded by neuronal membrane and it is possible in such a preparation to study a depolarization-induced opening of VOC. In the present model $^{45}$Ca influx is induced in the synaptosomes by depolarization with elevated potassium concentrations, and the effect of test substances on this stimulated uptake is studied (Nachshen, D.A. and Blaustein, M.P., Mol. Pharmcol., 16, 579 (1979)).

ASSAY

A male Wistar rat is decapitated and the cerebral cortex removed and homogenized in 20 ml. of ice-cold 0.32M sucrose using a glass homogenizer with a teflon pestle. All subsequent steps for isolation of synaptosomes are done at 0°–4° C. The homogenate is centrifuged at 1000×g for 10 min and the resulting supernatant is re-centrifuged at 18000×g for 20 min. This pellet ($P_2$) is resuspended in 0.32M sucrose (10 ml per g of original tissue) with a teflon pestle.

Aliquots (0.050 ml) of this crude synaptosomal suspension are added to glass tubes containing 0.625 ml of NaCl buffer (136 mM NaCl, 4 mM KCl, 0.35 mM $CaCl_2$, 1.2 mM $MgCl_2$, 20 mM Tris HCl, 12 mM glucose, pH 7.4) and 0.025 ml of various drug solutions in 48% Ethanol. The tubes are pre-incubated for 30 min on ice and then for 6 min at 37° C. in a water bath.

The uptake is immediately initiated by adding 0.4 ml of $^{45}CaCl_2$ (specific activity=29–39 Ci/g; 0.5 Ci/assay), in 145 mM NaCl for non-depolarized samples and in 145 mM KCl for depolarized samples. The incubation is continued for 15 s.

The uptake is terminated by rapid filtration through GF-C glass fiber filters which are washed three times with 5 ml of a cold solution containing 145 mM KCl, 7 mM EGTA and 20 mM Tris HCl, pH 7.4. The amount of radioactivity on the filter disc is determined by liquid scintillation spectrometry.

TEST PROCEDURE

Test substances are dissolved in 10 ml of 48% ethanol at a concentration of 0.44 mg/ml. Dilution are made in 48% ethanol to give final concentrations of 0.1, 0.3, 1, 3 and 10 μg/ml. Experiments are performed in duplicate. Controls for depolarized and nondepolarized samples are included in the assay and test substances are only tested in depolarized samples.

RESULTS

The test value will be given as MEC (the minimum concentration (μg/ml) of test substance which inhibit stimulated uptake of $^{45}Ca$ significantly different from control ($P<0.05$, Student's t-test).

Test results obtained by testing some compounds of the present invention will appear from the following table 1.

TABLE 1

| Compound | MEC (μg/ml) |
| --- | --- |
| 1 | 3.0 |
| 2 | 1.0 |
| 3 | 0.3 |
| 4 | 0.3 |
| 16 | 0.3 |
| 17 | 0.3 |
| 22 | >1.0 |
| Verapmil* | 10 |
| Nifedipin* | >10 |
| Diltiazem* | >10 |

*well known calcium antagonist

The compound of the invention, together with a conventional adjuvant, carrier, or, diluent, and if desired in the form of a pharmaceutically-aoceptable acid addition salt thereof, may be placed into the form of pharmaceutical compositions and unit dosages thereof, and in such form may be employed as solids, such as tablets or filled capsules, or liquids, such as solutions, suspensions, emulsions, elixirs, or capsules filled with the same, all for oral use, in the form of suppositories for rectal administration; or in the form of sterile injectable solutions for parenteral (including subcutaneous) use. Such pharmaceutical compositions and unit dosage forms thereof may comprise conventional ingredients in conventional proportions, with or without additional active compounds or principles, and such unit dosage forms may contain any suitable effective calcium overload blocking amount of the active ingredient commensurate with the intended daily dosage range to be employed. Tablets containing ten (10) milligrams of active ingredient or, more broadly, ten (10) to hundred (100) milligrams, per tablet, are accordingly suitable representative unit dosage forms.

The compounds of this invention can thus be used for the formulation of pharmaceutical preparations, e.g. for oral and parenteral administration to mammals including humans, in accordance with conventional methods of galenic pharmacy.

Conventional excipients are such pharmaceutically acceptable organic or inorganic carrier substances suitable for parenteral or enteral application which do not deleteriously react with the active compounds.

Examples of such carriers are water, salt solutions, alcohols, polyethylene glycols, polyhydroxyethoxylated castor oil, gelatine, lactose, amylose, magnesium stearate, talc, silicic acid fatty acid monoglycerides and diglycerides, pentaerythritol fatty acid esters, hydroxymethylcellulose and polyvinylpyrrolidone.

The pharmaceutical preparations can be sterilized and mixed, if desired, with auxiliary agents, emulsifiers, salt for influencing osmotic pressure, buffers and/or coloring substances and the like, which do not deleteriously react with the active compounds.

For parenteral application, particularly suitable are injectable solutions or suspensions, preferably aqueous solutions with the active compound dissolved in polyhydroxylated castor oil.

Ampoules are convenient unit dosage forms.

Tablets, dragees, or capsules having talc and/or a carbohydrate carrier or binder or the like, the carrier preferably being lactose and/or corn starch and/or potato starch, are particularly suitable for oral application. A syrup, elixir of the like can be used in cases where a sweetened vehicle can be employed.

Generally, the compounds of this invention are dispensed in unit form comprising 0.05–100 mg in a pharmaceutically acceptable carrier per unit dosage.

The dosage of the compounds according to this invention is 0.1–300 mg/day, preferably 10–100 mg/day, when administered to patients, e.g. humans, as a drug.

A typical tablet which may be prepared by conventional tabletting techniques contains:

| | |
| --- | --- |
| Active compound | 5.0 mg |
| Lactosum | 67.8 mg Ph. Eur. |
| Avicel ® | 31.4 mg |
| Amberlite ®IRP 88 | 1.0 mg |
| *Magnesii stearas* | 0.25 mg Ph. Eur. |

Due to the high calcium overload blocking activity, the compounds of the invention are extremely useful in the treatment of symptoms related to an accumulation of calcium in brain cells of mammals , when administered in an amount effective for blocking calcium overload in brain cells. The important calcium overload blocking activity of compounds of the invention includes both activity against anoxia, ischemia, migraine and epilepsy. The compounds of the invention may accordingly be administered to a subject, e.g., a living animal body, including a human, in need of a calcium overload blocker, and if desired in the form of a pharmaceutically-acceptable acid addition salt thereof (such as the hydrobromide, hydrochloride, or sulfate, in any event prepared in the usual or conventional manner, e.g., evaporation to dryness of the free base in solution together with the acid), ordinarily concurrently, simultaneously, or together with a pharmaceutically-acceptable carrier or diluent, especially and preferably in the form of a pharmaceutical composition thereof, whether by oral, rectal, or parenteral (including subcutaneous) route, in an effective calcium overload blocking amount, and in any event an amount which is effective for the treatment of anoxia, ischemia, migraine or epilepsy due to their calcium overload blocking activity. Suitable dosage ranges are 0.1-300 milligrams daily, preferably 10-100 milligrams daily, and especially 30-70 milligrams daily, depending as usual upon the exact mode of administration, form in which administered, the indication toward which the administration is directed the subject involved and the body weight of the subject involved, and the preference and experience of the physician or veterinarian in charge.

The invention will now be described in further detail with reference to the following examples:

EXAMPLE 1

(+−)N-methyl-N-pentyl-3-phenyl-3-(4-trifluoromethylphenoxy)propylamine, maleinate (Compound 1)

The title compound was prepared from (+−)-N-Methyl-N-(3-phenyl-3-(4-trifluoromethylphenoxy)-propyl)-amine, hydrochloride (1 g), potassium carbonate (2 g) and bromopentane (1 ml) by reflux in abs. ethanol (50 ml) for 40 h. The mixture was cooled, acetone/ether (1/1) (50 ml) was added and the mixture was filtered. The filtrate was evaporated to dryness and subsequently suspended in dilute NaOH-solution and extracted with ether. The ether layer was dried (MgSO$_4$) and evaporated to dryness. The title compound was precipitated as the maleinate in acetone solution. M.p. 99° C.

The following compounds were obtained in exactly the same way as above by reaction with the appropriate bromo compound instead of bromopentane.

(+−)N-methyl-3-phenyl-N-propyl-3-(4-trifluoromethylphenoxy)propyl, oxalate (Compound 2)

Reflux time 9 h. Precipitated as the oxalate in acetone solution. M.p. 167°-9° C.

(+−)N-butyl-N-methyl-3-phenyl-3-(4-trifluoromethylphenoxypropylamine, oxalate (Compound 3)

Reflux time 22 h. Purification of the free amine on a silicagel column using CH$_2$Cl$_2$ as eluent. Crystallized as the oxalate from acetone/ether. M.p. 160°-2° C.

(+−)N-cyclopropylmethyl-N-methyl-3-phenyl-3-(4-trifluoromethylphenoxypropylamine, oxalate (Compound 4)

Reflux time 4 h. The oxalate crystallized from acetone/ether. M.p. 148,4° C.

(+−)N-allyl-N-methyl-3-phenyl-3-(4-trifluoromethylphenoxy)propylamine, oxalate (Compound 5)

Equimolar amounts of amine and alkylbromide was used. Reflux time 1 h, RT 16 h. M.p. 104.5° C.

(+−)N-5-hexenyl-N-methyl-N-(3-phenyl-3-(4-trifluoromethylphenoxy)propylamine, oxalate (Compound 6)

Reflux time 19 h. The oxalate crystallized from acetone/ether. M.p. 126.1° C.

(+−)N-2-ethoxyethyl-N-methyl-3-phenyl-3-(4-trifluoromethylphenoxy)propylamine, oxalate (Compound 7)

Reflux time 120 h. M.p. 127.5° C.

(+−)N-methyl-N-(4-phenoxybutyl)-3-phenyl-3-(4-trifluoromethylphenoxy)propylamine, oxalate (Compound 8)

Reflux time 140 h. Purification of the free amine on a silicagel column using CH$_2$Cl$_2$/CH$_3$OH (9:1) as eluent. M.p. 95.7° C.

(+−)N-methyl-N-(2-methylpropyl)-3-phenyl-3-(4-trifluoromethylphenoxy)propylamine, oxalate (Compound 9)

Reflux time 48 h. Purification of the crude product on silicagel column using CH$_2$Cl$_2$/CH$_3$OH (9:1) as eluent. M.p. 169.5° C.

EXAMPLE 2

(+−)3-dimethylamino-1-phenyl-1-propanol (Compound 10)

β-dimethylaminopropiophenone (20.3 g) was dissolved in abs. ethanol, sodium borohydride (1.09 g) was added and the mixture was stirred at RT for 19 h. Subsequently the reaction mixture was evaporated to dryness; the residue was extracted with H$_2$O/diethylether. The combined etheral layers were dried (MgSO$_4$), filtration and evaporation gave (10) as a yellow oil identified by its $^1$H NMR spectrum.

(+−)3-chloro-N,N-dimethyl-3-phenylpropylamine, hydrochloride (Compound 11)

(+−)3-dimethylamino-1-phenyl-1-propanol (10) (19 g) was dissolved in CH$_2$Cl$_2$ (200 ml). The solution was saturated with HCl (g). Thionyl chloride (17 ml) was added dropwise over 20 min. resulting in slight reflux. Subsequental reflux for 5 h resulted in the formation of a precipitate. Cooling and evaporation of the reaction mixture resulted in a yellowish crystalline mass, which was rinsed by several washings with acetone, resulting in colourless crystals of the title compound identified by $^1$H NMR.

(+−)N,N-dimethyl-3-phenyl-3-(5,6,7,8-tetrahydro-2-naphthoxy)propylamine, oxalate (Compound 12)

5,6,7,8-tetrahydro-2-naphthol (7.4 g) and NaOH (2 g) was dissolved in abs. ethanol (100 ml) by stirring at RT. When all was dissolved compound (11) (6 g) was added and the mixture refluxed for 120 h. The mixture was evaporated to dryness, the residue extracted from 4M NaOH/diethylether. The combined ether layers were dried (MgSO$_4$), filtered and the filtrate evaporated to dryness yielding an oil. The oil was precipitated as the oxalate by mixing equimolar amounts of anhydrous oxalic acid and free amine. M.p. 164.4° C.

(+ —)N-methyl-3-phenyl-3-(5,6,7,8-tetrahydro-2-naphthoxy)-propylamine, oxalate (Compound 13)

Compound (12) as the free base (2 g) was dissolved in dry 1,2-dichloroethane (30 ml). 1-chloroethyl chloroformate (0.76 ml) was added dropwise under cooling. The solution was refluxed for 1 h, evaporated to dryness. Methanol (50 ml) was added, and the solution refluxed for 3 h. Subsequent evaporation, extraction from 4M NaOH/ether gave a yellow oil after evaporation of the ether layer. Precipitation in acetone solution by mixing equimolar amounts of amine and anhydrous oxalic acid. M.p. 190.2° C.

The following compounds were prepared from compound (13) as described in example 1, compound 1.

(+ —)N-methyl-N-pentyl-3-phenyl-3-(5,6,7,8-tetrahydro-2-naphthoxy)propylamine, oxalate (Compound 14)

Reflux time 7 h. M.p. 168.4° C.

(+ —)N-cyclopropylmethyl-N-methyl-3-phenyl-3-(5,6,7,8-tetrahydro-2-naphthoxy)propylamine, oxalate (Compound 15)

Reflux time 4.5 h. M.p. 134.8° C.

(+ —)N-butyl-N-methyl-3-phenyl-3-(5,6,7,8-tetrahydro-2-naphthoxy)propylamine, oxalate (Compound 16)

Reflux time 18 h. M.p. 160.8° C. Cl (+-)N-methyl-N-(2-methylpropyl)-3-phenyl-3-(5,6,7,8-tetrahydro-2-naphthoxy)propylamine, oxalate (Compound 17)

Reflux time 48 h. M.p. 153.2° C.

(+ —)N-methyl-3-phenyl-N-propyl-3-(5,6,7,8-tetrahydro-2-naphthoxy)propylamine, oxalate (Compound 34)

Reflux time 6 h. Purification on silica gel column with $CH_2Cl_2/CH_3OH$ (9:1) as eluent. M.p. 169.1°–169.7° C.

EXAMPLE 3

(+ —)N,N-dimethyl-3-(3,4-methylenedioxyphenoxy)-3-phenylpropylamine, oxalate (Compound 18)

Preparation from compound (11) and 3,4-methylenedioxyphenol as described for compound (12). M.p. 96.9° C.

(+ —)N-methyl-3-(3,4methylenedioxyphenoxy)-3-phenylpropylamine, oxalate (Compound 19)

Preparation from (18) and $ClCOOCHClCH_3$ as described for compound (13) with the exception that sodium dried toluene was used as solvent instead of 1,2-dichloroethane. Heating in toluene at 80° C. for 2 h. M.p. 148.7° C.

(+ —)N-cyclopropylmethyl-N-methyl-3-(3,4-methylenedioxyphenoxy)-3-pheny lpropylamine, oxalate (Compound 20)

Prepared from compound (19) and bromomethylcyclopropane using the method described for compound (1). Reflux time 4.5 h. M.p., 150.O° C.

(+ —)N-butyl-N-methyl-3-(3,4-methylenedioxyphenoxy)-3-phenylpropylamine, oxalate (Compound 21)

Preparation from compound (19) and 1-bromobutane as described for compound (1). Reflux time 19 h. M.p. 127.0° C.

EXAMPLE 4

(+ —)3-(5-indanyloxy)-N,N-dimethyl-3-phenylpropylamine, oxalate (Compound 22)

Prepared from compound (11) and 5-indanol by reflux for 75 h as described for compound (12). M.p. 153.2° C.

(+ —)3-(5-indanyloxy)-N-methyl-3-phenylpropylamine, oxalate (Compound 23)

Preparation from compound (22) and $ClCOOCHClCH_3$ as described for compound (19). M.p. 161.4° C.

(+ —)N-butyl-3-(5-indanyloxy)-N-methyl-3-phenylpropylamine, oxalate (Compound 24)

Prepared from compound (23) and 1-bromobutane as described for compound (1). M.p. 172.5° C.

(+ —)N-cyclopropylmethyl-3-(5-indanyloxy)-N-methyl-3-phenylpropylamine, oxalate (Compound 25)

Prepared from compound (23) and bromomethylcyclopropane as described for compound (1). M.p. 175.8° C.

EXAMPLE 5

(+ —)N,N-dimethyl-3-phenyl-3-(3-trifluoromethylphenoxy)propylamine, oxalate (Compound 26)

Prepared from compound (11) and 3-trifluoromethylphenol by reflux for 75 h, as described for compound (12). M.p. 167.7° C.

(+ —)N-methyl-3-phenyl-3-(3-trifluoromethylphenoxy)propylamine, oxalate (Compound 27)

Prepared from compound (26) by means of $ClCOOCHClCH_3$ as desribed for compound (19). M.p. 157.7° C.

(+-)N-butyl-N-methyl-3-phenyl-3-(3-trifluoromethylphenoxy)propylamine, oxalate (Compound 28)

Preparation as described for compound (1) from 1-bromobutane and (27). M.p. 153.2° C.

(+ —)N-cyclopropylmethyl-N-methyl-3-phenyl-3-(3-trifluoromethylphenoxy)propylamine, oxalate (Compound 29)

Prepared from compound (27) and bromomethylcyclopropane as described under (1). M.p. 150.6° C.

EXAMPLE 6

(+ —)3-(2-cyanophenoxy)-N,N-dimethyl-3-phenylpropylamine, oxalate (Compound 30)

The compound was prepared from (11) and 2-cyanophenol as described for (12) by reflux for 10 h. M.p. 138°–43° C.

EXAMPLE 7

(+ —)N,N-dimethyl-3-(2-methylphenoxy)-3-phenylpropylamine, oxalate (Compound 31)

Preparation from (11) and 2-methylphenol by reflux for 27 h as described for compound (12). M.p. 169°–171° C.

EXAMPLE 8

(+ —)3-(2-methoxyphenoxy)-N,N-dimethyl-3-phenyl-propylamine, oxalate (Compound 32)

Preparation from (11) and 2-methoxyphenol by reflux for 1 h as described for compound (12). M.p. 127°–130° C.

(+ —)N-butyl-N-methyl-3-(2-methoxyphenoxy)-3-phenylpropylamine, oxalate (Compound 33)

Prepared from N-methyl-3-(2-methoxyphenoxy)-3-phenylpropylamine and 1-bromobutane by reflux in ethanol solution for 10 h as described for compound (1). M.p. 102°–6° C.

We claim:

1. A method of treating an indication related to calcium overload in brain cells of mammals, including humans, in a subject in need thereof, which comprises the step of administering to the said subject a calcium overload blocking amount of a compound selected from those having the formula

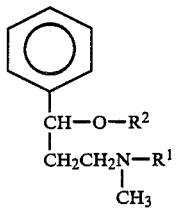
(I)

wherein
$R^1$ is H, $C_{3-7}$-cycloalkyl, $C_{1-10}$-alkyl or alkenyl which may be straight, branched or cyclic, unsubstituted or substituted with $C_{1-4}$-alkoxy, aryloxy or cycloalkyl or cycloalkylalkyl; and
$R^2$ is 3,4-methylenedioxyphenyl, up to and including aryl or C10 which are optionally substituted with one or more halogen, $C_{1-6}$-alkyl, $C_{1-6}$-alkoxy, $C_{2-6}$-alkenyl, trifluoromethyl, $C_{3-5}$-alkylene, up to C10 aryloxy, or up to C10 aralkoxy,
and a salt thereof with a pharmaceutically acceptable acid.

2. Method of claim 1 wherein the compound is N-butyl-N-methyl-3-phenyl-3-(4-trimethylphenoxy)-propylamine.

3. Method of claim 1 wherein the compound is N-cyclopropylmethyl-N-methyl-3-phenyl-3-(4-trifluoromethylphenoxy)propylamine.

4. Method of claim 1 wherein the compound is N-butyl-N-methyl-3-phenyl-3-(5,6,7,8-tetrahydro-2-naphthoxy)propylamine.

5. Method of claim 1 wherein the compound is N-butyl-3-(5-indanyloxy)-N-methyl-3-phenylpropylamine.

6. Method of claim 1 wherein the compound is N-cyclopropyl-N-methyl-3-phenyl-3-(3-trifluoromethylphenoxy)propylamine.

* * * * *

UNITED STATES PATENT AND TRADEMARK OFFICE
CERTIFICATE OF CORRECTION

PATENT NO. : 4,970,232

DATED : Nov. 13, 1990

INVENTOR(S) : Palle Jakobsen, Jørgen Drejer

It is certified that error appears in the above-identified patent and that said Letters Patent is hereby corrected as shown below:

```
Column 2, line 11; delete "the", second occurrence.
Column 2, line 57; "socalled" should read -- so-called --.
Column 2, line 60; "socalled" should read -- so-called --.
Column 3, line 33; "Dilution are" should read -- Dilution is --.
Column 3, TABLE I, first column, 8th line down; "Verapmil*"
    should read -- Verapamil* --.
Column 3, line 62; "or, diluent," should read -- or diluent, --.
Column 3, line 63: "pharmaceutically-aoceptable" should read
    -- pharmaceutically-acceptable --.
Column 4, line 12; "to hundred" should read -- to one hundred --.
Column 4, approximate line 27/28; "acid fatty" should read
    -- acid, fatty --.
Column 5, approximate line 25; "directed the" should read
    -- directed, the --.
Column 7, approximate line 47; "4methylenedioxyphenoxy" should
    read -- 4-methylenedioxyphenoxy --.
Column 10, line 15; "aryloxy or" should read
    -- aryloxy, or --.
```

UNITED STATES PATENT AND TRADEMARK OFFICE
CERTIFICATE OF CORRECTION

PATENT NO.  : 4,970,232

DATED       : Nov. 13, 1990

INVENTOR(S) : Palle Jakobsen, Jørgen Drejer

It is certified that error appears in the above-identified patent and that said Letters Patent is hereby corrected as shown below:

Column 10, line 17; "methylenedioxyphenyl, up" should read
-- methylenedioxyphenyl, or up --.
Column 10, line 17/18; "including aryl" should read
-- including C10 aryl, --.
Column 10, line 18; delete "or C10".
Column 10, line 25; "(4-trimethylphenoxy)" should read
-- (4-trifluoromethylphenoxy) --.

Signed and Sealed this

Second Day of June, 1992

*Attest:*

DOUGLAS B. COMER

*Attesting Officer*         Acting Commissioner of Patents and Trademarks